United States Patent [19]
Buser

[11] Patent Number: 5,810,750
[45] Date of Patent: Sep. 22, 1998

[54] METHOD FOR ALIGNING A FRACTURED BONE

[76] Inventor: John Paul Buser, 837 Cornish Dr., San Diego, Calif. 92107

[21] Appl. No.: 864,213

[22] Filed: May 24, 1997

Related U.S. Application Data

[63] Continuation-in-part of Ser. No. 519,487, Aug. 25, 1995, abandoned.

[51] Int. Cl.⁶ ........................................................ A61F 5/00
[52] U.S. Cl. ............................ 602/13; 128/898; 602/36; 602/39; 606/86
[58] Field of Search .................................. 602/5, 13, 32, 602/36, 38, 39, 40, 63; 606/53, 54, 57, 86, 105

[56] References Cited

U.S. PATENT DOCUMENTS

| | | |
|---|---|---|
| 2,245,909 | 6/1941 | Enfiajian . |
| 2,823,668 | 2/1958 | Van Court et al. . |
| 2,943,859 | 7/1960 | Koski et al. . |
| 3,164,152 | 1/1965 | Nicoll . |
| 3,403,676 | 10/1968 | Gibbons . |
| 3,654,919 | 4/1972 | Birtwell . |
| 3,701,349 | 10/1972 | Larson . |
| 3,771,519 | 11/1973 | Haake . |
| 3,868,952 | 3/1975 | Hatton . |
| 4,157,713 | 6/1979 | Clarey . |
| 4,266,298 | 5/1981 | Graziano . |
| 4,338,923 | 7/1982 | Gelfer et al. . |
| 4,621,624 | 11/1986 | Rayboy . |
| 4,862,879 | 9/1989 | Coombs . |
| 5,014,681 | 5/1991 | Neeman et al. . |
| 5,042,508 | 8/1991 | Richard ..................................... 128/882 |
| 5,171,310 | 12/1992 | Chisena ........................................ 602/5 |
| 5,267,951 | 12/1993 | Ishii . |
| 5,288,286 | 2/1994 | Davis et al. . |
| 5,376,067 | 12/1994 | Daneshvar . |
| 5,718,669 | 2/1998 | Marble ........................................ 602/5 |

FOREIGN PATENT DOCUMENTS 2553996  3/1985  France .

*Primary Examiner*—Linda C. Dvorak
*Attorney, Agent, or Firm*—Nydegger & Associates

[57] ABSTRACT

The present invention provides a method for aligning a fractured bone in a limb of a patient. The method includes positioning on the limb two pairs of selectively inflatable bladders formed in a flexible wrap. Each bladder is oblong shaped and is oriented with the longitudinal axis of the bladder parallel to the longitudinal axis of the bone. The flexible wrap is secured around the limb to position the bladders on the limb over the fractured bone. The two bladders of each pair of bladders are positioned on the limb in a radially opposed orientation. Further, all of the bladders are radially distributed at 90 degree intervals around the limb. The bladders are selectively inflated to generate forces between the wrap and the limb, which act in concert to align the bone. The forces include a direct force between each bladder and the limb that transitions from being substantially concentrated to being substantially uniformly distributed during realignment of the bone. Once the bone is aligned, an intramedullary nail may be inserted into the bone to stabilize the bone during the healing of the bone.

20 Claims, 2 Drawing Sheets

METHOD FOR ALIGNING A FRACTURED BONE

This application is a continuation in part of application Ser. No. 08/519,487, filed Aug. 25, 1995, which is now abandoned. The contents of application Ser. No. 08/519,487 are incorporated herein by reference.

FIELD OF THE INVENTION

The present invention pertains generally to medical methods for treating bone fractures in patients. More particularly, the present invention pertains to methods which are useful for aligning a fractured bone in a patient. The present invention is particularly, but not exclusively, useful as a method for aligning a fractured bone in a patient to facilitate insertion of an intramedullary nail into the bone.

BACKGROUND OF THE INVENTION

When a bone in a patient is fractured, it is widely known that one of the first steps of medical treatment is to align the bone to the bone's pre-fracture configuration. This alignment of the bone facilitates healing and diminishes the possibility of deformity of the bone. Once the bone has been aligned, medical procedures, such as 'rodding,' may be used to maintain the alignment of the bone during the healing process.

The process of 'rodding,' whereby a specially designed rod or nail is inserted to support a fractured bone is well known in the medical arts. In fact, the use of rods or nails to repair skeletal fractures dates back to at least 1841 when ivory pegs were used in a manner somewhat suggestive of the current practice. Generally, repairs of this type involve a technique known as intramedullary, or IM, nailing where a nail is inserted to follow the intramedullary canal of the fractured bone.

Typically, IM nailing has been performed when the required repair site is located within the femur, tibia or humerus. In such cases, it may be appreciated that the size of the bone and the size of the intramedullary canal are generally large enough to allow insertion of a properly dimensioned nail while still leaving adequate supporting material around the site of insertion. Additionally, the anatomical location of the femur, tibia or humerus within the major limbs facilitates manipulation of the bones during the nailing procedure. As a result, insertion of IM nails within these bones has been found to be both therapeutic and practical.

Insertion of an IM nail within a skeletal bone, such as the femur, tibia or humerus, is generally performed by first placing the patient on a fracture table. Next, a series of manual manipulations may be applied to the involved limb to realign the bone segments at the fracture site. As these manipulations are performed, it is often advantageous for an X-ray image of the fracture site to be generated. The X-ray image may be consulted to determine whether the manual manipulations have succeeded in correctly placing the fractured bone into proper anatomical alignment. The steps of manual manipulation and X-ray imaging may then be repeated until the proper anatomical alignment exists at the fracture site.

After the fracture has been correctly aligned, an incision is made which allows access to one of the ends of the involved bone. For instance, in cases where the fracture site lies within the patient's femur, an incision is made through the gluteus maximus allowing access to the proximal tip of the greater trochanter. Alternatively, in cases where the fracture site is located within the patient's tibia, an incision is made on the medial side of the patellar ligament to allow access to the tibial tuberosity.

Once access to the proper end of the involved bone has been established, various boring and reaming instruments may be used to establish a pilot hole or bore within the intramedullary canal of the particular bone involved. It is of critical importance that the fracture site be maintained in proper anatomical alignment as the pilot hole is established. In particular, it may be appreciated that misalignment of the pilot hole may result in improper bone alignment as the IM nail is inserted and may even result in incorrect healing of the fracture site.

The establishment of the pilot hole is followed by insertion of the IM nail into the intramedullary canal. As the nail is inserted, it passes between the disjoint segments of the fractured bone, holding the segments together into a single piece. Once again, it is of critical importance that the alignment of the fractured bone be maintained during the insertion of the IM nail both to ease the effort required for insertion as well as to reduce the force and resulting trauma associated with the insertion process.

The process of IM nailing is not without associated problems. In particular, it is easily appreciated that the necessity of establishing and maintaining the fractured bone in proper anatomical alignment adds complexity and generally slows the process of IM nailing. Worse, failure to establish and maintain proper alignment may result in serious side effects including improper healing of the fracture site. As a result, various techniques have been developed for establishing proper anatomical alignment of the bone.

One common method of alignment has been to have a surgical assistant or assistants manually hold and position the limb of the patient during the nailing procedure. Unfortunately, this method suffers from a general lack of precision. Additionally, the use of manual force makes the employment of X-ray imaging problematic both in terms of excess exposure of the assistants to radiation hazards as well as the difficulty in gathering an unobstructed image of the fracture site.

Another common practice has been to employ a tractive positioning system to apply an aligning force. The tractive system eliminates much of the lack of precision associated with manual positioning. Unfortunately, however, the presence of the tractive apparatus may interfere with the gathering of an unobstructed X-ray image. The use of tractive alignment may also require direct attachment of the tractive apparatus to the fractured bone with the result that additional incisions may be required. As a result, the use of tractive alignment may, in some cases, actually slow the process of patient recovery.

Experience has proven that the efficacy of any surgical procedure may be severely degraded if sterile conditions are not maintained. This importance of sterile conditions is especially relevant to IM nailing procedures due to the presence of various incisions in the effected limb. These incisions result, of course, from the IM nailing and tractive techniques applied to the effected limb. Additionally, the effected limb may have various incisions or other injuries created traumatically at the time the fracture was created. The presence of incisions or injuries on the effected limb creates a path for infection and resulting illness. As a result, it is highly desirable that the procedures used for alignment of the bone, and for maintaining the alignment of the bone during the IM nailing process, do not require additional incisions and that they maintain a sterile environment to reduce the chance of infection or disease.

Experience has also demonstrated that the efficacy of many medical procedures may be enhanced by increasing the speed with which the procedure is performed. By increasing the speed of a given procedure, the duration of the procedure and, in particular, the duration of the patient's exposure to anesthesia is reduced. Reduction in procedure time and anesthesia exposure is generally regarded as being advantageous to the health of the patient. Reduction in procedure time may also decrease the cost associated with the procedure.

In light of the above, it is an object of the present invention to provide a method for aligning a fractured bone in a correct anatomical orientation. Another object of the present invention is to provide a method for aligning a fractured bone which will reliably maintain the anatomical alignment of the fractured bone during the insertion of an IM nail. Still another object of the present invention is to provide a method for aligning a fractured bone that permits obtaining unobstructed X-ray images of the bone during and after the alignment process. Yet another object of the present invention is to provide a method for aligning a fractured bone which reduces the physical trauma experienced by the patient as the fractured bone is placed into alignment. Another object of the present invention is to provide a method for aligning a fractured bone that does not require incisions and that maintains a sterile environment to reduce the risk of infection to the patient. Another object of the present invention is to provide a method for aligning a fractured bone that permits alignment of the bone relatively quickly. Still another object of the present invention is to save operating time and reduce hospital expenses by providing a method for aligning a fractured bone which does not require repeated manipulations. Yet another object of the present invention is to provide a method for aligning a fractured bone which is relatively simple, and comparatively cost effective.

SUMMARY OF THE PREFERRED EMBODIMENTS

A method for aligning a fractured bone in a limb of a patient includes positioning two pairs of selectively inflatable bladders on the limb. The bladders are formed in a flexible wrap which is secured around the limb to position the bladders on the limb over the fractured bone. Each bladder is oblong shaped, and is oriented on the limb with the longitudinal axis of the bladder parallel to the longitudinal axis of the bone. Two of the bladders referred to as the anterior-posterior pair of bladders, are positioned on the limb in a radially opposed orientation, one hundred and eighty degrees (180°) apart around the bone. Similarly, the other two bladders, referred to as the medial-lateral pair of bladders, are also positioned on the limb in a radially opposed orientation, one hundred and eighty degrees (180°) apart around the bone. Further, the anterior-posterior pair of bladders are each oriented around the bone ninety degrees (90°) from each of the medial-lateral bladders.

With the wrap secured around the limb, any number of the bladders are inflated with a suitable fluid, such as air, to generate forces between the wrap and the limb. When inflated, the anterior-posterior pair of bladders generate radially opposed forces against the limb to align the bone. Similarly, when inflated, the medial-lateral pair of bladders generate radially opposed forces against the limb to align the bone. Due to the orientation of the bladders around the limb, the forces generated by the anterior-posterior pair of bladders are directed perpendicular to the forces generated by the medial-lateral pair of bladders. The forces generated by the inflated bladders act in concert to align the bone. As each bladder is inflated, the forces generated by the bladder include a direct force between the bladder and the limb that transitions from a substantially concentrated force against the bone to a substantially uniformly distributed force. The force transitions from concentrated to uniformly distributed as protrusions of the bone that are generally perpendicular to the longitudinal axis of the bone are minimized as the bone is straightened due to the inflation of the bladders.

The bladders and the flexible wrap are made of material which is substantially transparent to X-rays. This permits obtaining X-ray images of the bone with the bladders secured to the patient. An X-ray image of the bone may be obtained after the bladders have been inflated. If obtained, the X-ray image is analyzed to determine if additional forces need to be applied to further align the bone. If so, each bladder is then inflated or deflated as needed to produce the desired forces on the bone. This process of obtaining an X-ray image and further inflating or deflating the bladders may be repeated as many times as is necessary to achieve satisfactory alignment of the bone.

After the bone is satisfactorily aligned, a procedure for maintaining the alignment of the bone during the healing process may be performed, such as inserting an intramedullary nail into the bone to stabilize the bone. During the IM nailing process, proper alignment of the fracture site is maintained by the bladders and the flexible wrap. After completion of the IM nailing process, the bladders are deflated and the bladders and the wrap are removed from the patient.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
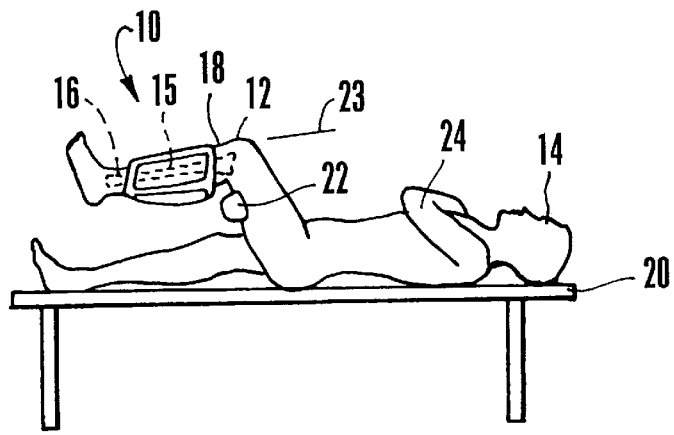
FIG. 1 is a side elevational view of an alignment device positioned around a leg of a patient during practice of the method of the present invention in the environment where the method is practiced.

An alignment device 10 for use in accordance with the method of the present invention is shown in FIG. 1 in its operational environment and is generally designated 10. As shown, the alignment device 10 has been applied over a limb 12 of a patient 14 for the purpose of anatomically aligning a fracture 15 within a tibia bone 16 of a leg 18 of the patient 14. In order to more easily align the bone 16, the patient 14 is positioned on a fracture table 20 with a leg support 22. After the bone 16 has been correctly aligned, an intramedullary nail 23 may be inserted into the bone 16 to maintain proper alignment of the bone 16 while the bone 16 heals. It will be appreciated that the method of the present invention can be practiced on other limbs, for example on an arm 24 of the patient 14. Generally, the method may be used to treat fractures within other skeletal bones, for example the femur, tibia, and humerus.

Figure 2:
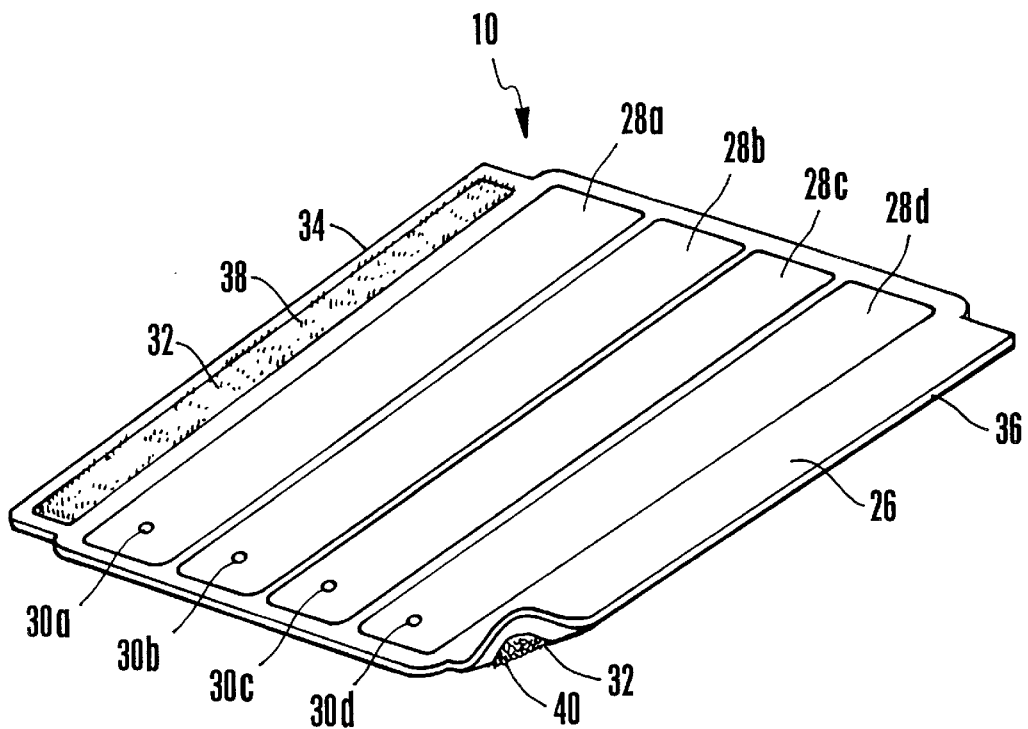
FIG. 2 is a perspective view of an alignment device used to practice the method of the present invention with the alignment device in a flat configuration.
Figure 3:
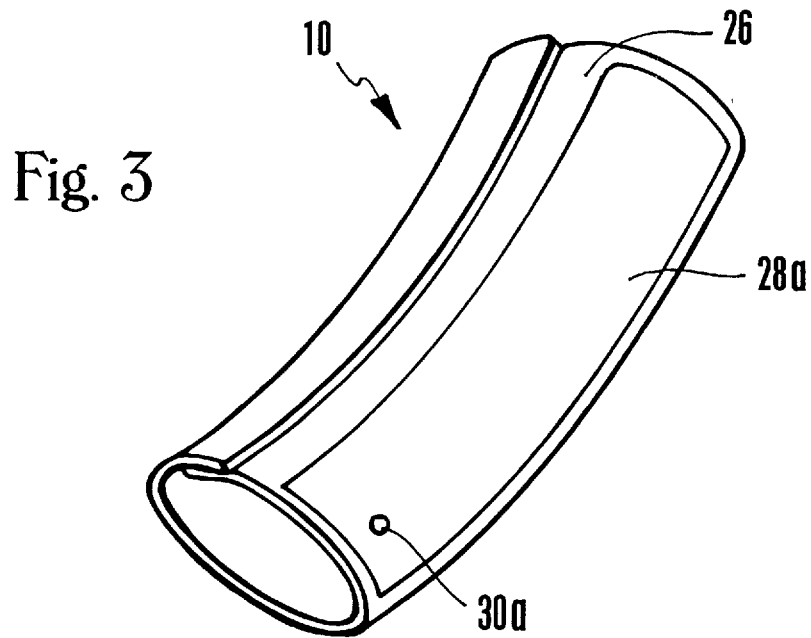
FIG. 3 is a perspective view of an alignment device used to practice the method of the present invention with the alignment device in a wrapped configuration.

Referring to FIG. 2, the alignment device 10 can be seen in more detail. The alignment device 10 includes a flexible wrap 26 and four selectively inflatable oblong shaped bladders 28a–d formed inside the flexible wrap 26. The flexible wrap 26 and the bladders 28a–d are formed from material which is flexible, sterilizable, and transparent to X-ray radiation, for example fiber impregnated vinyl. A quick release valve 30a–d is connected in fluid communication with each bladder 28a–d respectively, for independently inflating the bladders 28a–d. The flexible wrap 26 includes a connector 32, to connect edges 34, 36 of the flexible wrap 26 together. In this embodiment of the alignment device 10 the connector 32 includes hooks 38 and loops 40, which are secured to each other to hold the alignment device 10 in a wrapped, cylindrical configuration as shown in FIG. 3.

Figure 4:
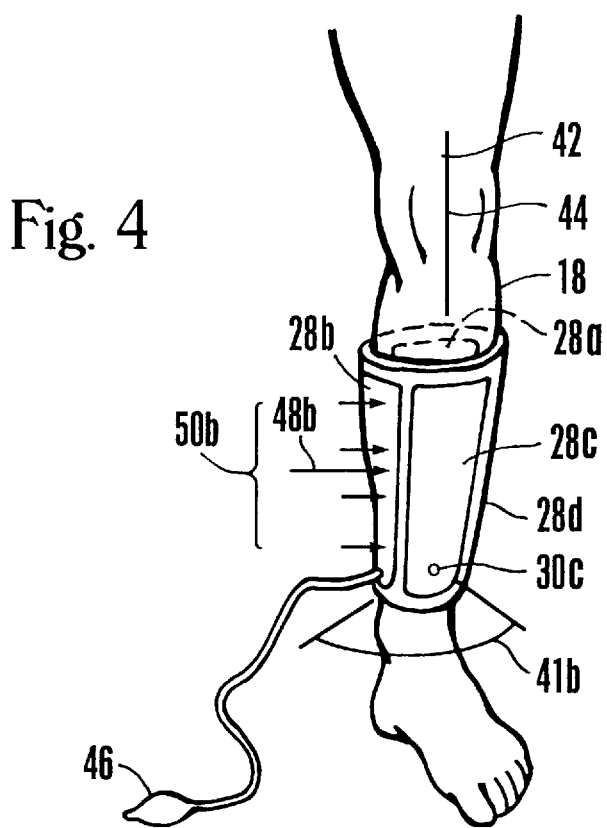
FIG. 4 is a perspective view of an alignment device positioned around a leg of a patient during practice of the method of the present invention.

Referring to FIG. 4, the method of the present invention for aligning the fractured bone 16 within the limb 12 of the patient 14 includes positioning bladder 28a in a radially opposed orientation to bladder 28c, and bladder 28b in a radially opposed orientation to bladder 28d on the leg 18 over the fractured bone 16. Additionally, bladders 28a–c are each positioned around the leg 18 separated by a respective angle 41a–d of about ninety degrees (90°) from each neighboring bladder 28b–d, as illustrated by angle 41b which is representative of similar angles 41a, 41c, and 41d. Further, the bladders 28a–d are positioned with the longitudinal axis 42 of each bladder 28a–d aligned substantially parallel with the longitudinal axis 44 of the bone 16. After the bladders 28a–d are correctly positioned around the leg 18, the hooks 38 of the connector 32 are affixed to the loops 40 of the connector 32 to secure the flexible wrap 26 around the leg 18, and to secure and maintain the bladders 28a–d in the positions described above. The alignment device 10 is shown correctly positioned around the leg 18 in FIG. 4.

After the bladders 28a–d are correctly positioned around the leg 18, the bladders 28a–d are selectively inflated to realign the bone. Inflation of a bladder 28a–d is accomplished by attaching a pump 46 to the respective quick release valve 30a–d attached to the bladder 28a–d to be inflated, and then repeatedly squeezing the pump. Those skilled in the art will appreciate that the method of the present invention can also be practiced by inflating the bladders 28a–d with other fluids, such as water.

After the flexible wrap 26 is secured around the leg 18, at least one bladder 28a–d is inflated to increase the pressure within the bladder 28a–d. Increasing the pressure in a bladder 28a–d generates forces between the flexible wrap 26 and the leg 18 for realigning the fractured bone 16. When inflated, bladders 28a and 28c generate radially opposed forces against the leg 18 to align the bone 16. Similarly, when inflated, bladders 28b and 28d also generate radially opposed forces against the leg 18 to align the bone 16. Due to the orientation of the bladders 28a–d around the leg 18, the forces generated by bladders 28a and 28c are directed perpendicular to the forces generated by bladders 28b and 28d. The forces generated by the inflated bladders 28a–d act in concert to align the bone 16.

The forces generated by each bladder 28a–d include a direct force between the bladder 28a–d and the leg 18. As a bladder 28a–d is inflated, the direct force transitions from a substantially concentrated force 48a–d to a substantially uniformly distributed force 50a–d against the bone 16. Forces 48b and 50b shown in FIG. 4 are representative of the forces 48a–d and 50a–d. The force transitions as protrusions of the bone 16 are minimized. Due to the fracture 15 in the bone 16, parts of the bone 16 may protrude in a direction generally perpendicular to the longitudinal axis 44 of the bone 16. Each concentrated force 48a–d is directed against these protrusions. The force transitions from being concentrated to being uniformly distributed as the protrusions are minimized as the bone 16 is straightened due to the inflation of the bladders 28a–d. In some instances, the force may be uniformly distributed throughout the inflation of a bladder 28a–d, if the bladder 28a–d is not positioned adjacent a protrusion of the bone 16. Each uniformly distributed force 50a–d is distributed along the longitudinal axis 44 of the bone 16 and is directed towards the bone 16 generally perpendicular to the longitudinal axis of 44 of the bone 16.

After the bladders 28a–d have been inflated, an X-ray may be taken of the bone 16, which is analyzed to determine the alignment of the bone 16. The magnitude and/or the direction of the aligning forces produced by the bladders 28a–d may be adjusted by increasing or decreasing the pressures in selected bladders 28a–d to improve the alignment of the bone 16. The pressure is increased by attaching the pump 46 to the appropriate quick release valve 30a–d and then repeatedly squeezing the pump. The pressure is decreased by pressing on a pressure release pin (not shown) on the appropriate valve 30a–d to release air from the selected bladder 28a–d. This process of obtaining an X-ray image and further inflating or deflating the bladders 28a–d may be repeated as many times as is necessary to achieve satisfactory alignment of the bone 16. If desired, the pressure in the bladders 28a–d may also be initially adjusted prior to taking an X-ray of the bone 16. Further, after the bladders 28a–d have been inflated, the pressure in the bladders 28a–d may be adjusted to maintain proper anatomical alignment of the bone 16.

After the bone 16 is satisfactorily aligned, a procedure for maintaining the alignment of the bone 16 during the healing process may be performed, such as inserting the intramedullary nail 23 into the bone 16 to stabilize the bone 16. During the intramedullary nailing process, proper alignment of the bone16 is maintained by the bladders 28a–d and the flexible wrap 26. After completion of the intramedullary nailing process, the bladders 28a–d are deflated and the bladders 28a–d and the wrap 26 are removed from the leg 18 of the patient 14.

While the particular method for aligning a fractured bone within the limb of a patient as herein shown and disclosed in detail is fully capable of obtaining the objects and providing the advantages herein before stated, it is to be understood that it is merely illustrative of the presently preferred embodiments of the method of the present invention and that no limitations are intended to the details of the method or the construction or design herein shown other than as described in the appended claims.

What is claimed is:

1. A method for aligning a fractured bone within the limb of a patient which comprises the steps of:

positioning a pair of selectively inflatable bladders in a radially opposed orientation on said limb over said fractured bone, said bladders being formed in a flexible wrap and positionable in said radially opposed orientation when said wrap is secured around said limb; and inflating at least one said bladder to increase pressure therein to generate forces between said wrap and said limb for realigning said fractured bone, said inflating step establishing a direct force between said bladder and said limb with said direct force transitioning from a substantially concentrated force against the bone to a substantially uniformly distributed force during realignment of the bone.

2. A method as recited in claim 1 further comprising the step of adjusting pressure in at least one said bladder after said inflating step to establish forces by said wrap on said limb for maintaining proper anatomical alignment of said fractured bone.

3. A method as recited in claim 2 wherein said adjusting step is accomplished by decreasing pressure in at least one said bladder.

4. A method as recited in claim 1 wherein said positioning step further comprises positioning an additional pair of selectively inflatable bladders in a radially opposed orientation on said limb over said fractured bone, said additional bladders being formed in said flexible wrap and positionable in said radially opposed orientation when said wrap is secured around said limb, said orientation of said additional pair of bladders being substantially perpendicular to said orientation of said pair of bladders on said limb.

5. A method as recited in claim 4 wherein each bladder of said pair of bladders and each bladder of said additional pair of bladders is generally oblong shaped, and wherein said positioning step includes aligning the longitudinal axis of each said bladder substantially parallel with the longitudinal axis of the bone.

6. A method as recited in claim 4 wherein each bladder of said pair of bladders and each bladder of said additional pair of bladders and said flexible wrap are substantially transparent to X-rays, and further comprising the steps of:

creating an X-ray image of the bone;

analyzing the alignment of the bone in said X-ray image; and changing the amount of inflation of at least one said bladder to improve the alignment of the bone.

7. A method as recited in claim 4 wherein said bladders and said flexible wrap are made of fiber impregnated vinyl.

8. A method as recited in claim 1 further comprising the step of inserting an intramedullary nail into said bone after said inflating step.

9. A method for aligning a fractured bone within the limb of a patient which comprises the steps of:

securing a flexible wrap around said limb; and providing means on said flexible wrap for generating a pair of radially opposed direct forces between said wrap and said limb for realigning said fractured bone, said forces initially being substantially concentrated and transitioning to being substantially uniformly distributed during realignment of the bone.

10. A method as recited in claim 9 wherein said means for generating a pair of radially opposed direct forces between said wrap and said limb is a pair of selectively inflatable bladders secured to said wrap in a radially opposed orientation on said limb over said fractured bone, said bladders being selectively inflated to generate said forces.

11. A method as recited in claim 10 further comprising the step of adjusting pressure in at least one said bladder after said inflating step to establish forces on said limb for maintaining proper anatomical alignment of said fractured bone.

12. A method as recited in claim 11 wherein said adjusting step is accomplished by decreasing pressure in at least one said bladder.

13. A method as recited in claim 9 further comprising means for generating an additional pair of radially opposed direct forces between said wrap and said limb for realigning said fractured bone, said additional forces initially being substantially concentrated and transitioning to being substantially uniformly distributed during realignment of the bone.

14. A method as recited in claim 13 wherein said additional pair of forces are directed substantially perpendicular to said pair of forces.

15. A method as recited in claim 13 wherein said means for generating a pair of radially opposed direct forces is a pair of selectively inflatable bladders secured to said wrap in a radially opposed orientation on said limb over said fractured bone selectively inflated to generate said forces and wherein said means for generating an additional pair of radially opposed direct forces is an additional pair of selectively inflatable bladders secured to said wrap in a radially opposed orientation on said limb over said fractured bone selectively inflated to generate said additional forces.

16. A method as recited in claim 15 wherein said pair of bladders and said additional pair of bladders are formed in said flexible wrap.

17. A method as recited in claim 15 wherein each bladder of said pair of bladders and each bladder of said additional pair of bladders is generally oblong shaped, and wherein said providing step includes aligning the longitudinal axis of each said bladder substantially parallel with the longitudinal axis of the bone.

18. A method as recited in claim 15 wherein said bladders and said flexible wrap are made of fiber impregnated vinyl.

19. A method as recited in claim 15 wherein said flexible wrap, and said means for generating a pair of radially opposed direct forces between said wrap and said limb, and said means for generating an additional pair of radially opposed direct forces between said wrap and said limb, are substantially transparent to X-rays, and further comprising the steps of:

creating an X-ray image of the bone;

analyzing the alignment of the bone in said X-ray image; and changing said forces to improve the alignment of the bone.

20. A method as recited in claim 9 further comprising the step of inserting an intramedullary nail into said bone.

* * * * *